United States Patent
Horner et al.

(10) Patent No.: US 8,568,397 B2
(45) Date of Patent: Oct. 29, 2013

(54) INDUCTION SEALING (75) Inventors: Glenn A. Horner, Boulder, CO (US);
Jeffrey M. Roy, Boulder, CO (US)

(73) Assignee: Covidien LP, Mansfield, MA (US)

( * ) Notice: Subject to any disclaimer, the term of this patent is extended or adjusted under 35 U.S.C. 154(b) by 758 days.

(21) Appl. No.: 12/769,444

(22) Filed: Apr. 28, 2010

(65) Prior Publication Data
US 2011/0270250 A1  Nov. 3, 2011

(51) Int. Cl.
A61B 18/04 (2006.01)
A61F 2/00 (2006.01)

(52) U.S. Cl.
USPC .................. 606/28; 606/27; 607/103

(58) Field of Classification Search
USPC ............... 606/27–28, 31, 50–52; 607/96–114
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D348,930 S | 7/1994 | Olson |
| D384,413 S | 9/1997 | Zlock et al. |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D493,888 S | 8/2004 | Reschke |
| D496,997 S | 10/2004 | Dycus et al. |
| D499,181 S | 11/2004 | Dycus et al. |
| 6,932,816 B2 | 8/2005 | Phan |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,588,565 B2 | 9/2009 | Marchitto et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Linda Dvorak
*Assistant Examiner* — Jaymi Della (57) ABSTRACT

An end effector assembly for use with an electrosurgical instrument is provided. The end effector assembly has a first jaw member having a support base and a sealing plate formed from a ferrous material. The end effector assembly also has a second jaw member including a support base, an electrical jaw lead and a sealing plate coupled to the electrical jaw lead. The sealing plate includes a first layer formed from a non-stick material and a second layer having a coil formed thereon.

8 Claims, 7 Drawing Sheets

(56) References Cited

U.S. PATENT DOCUMENTS

| | | | |
|---|---|---|---|
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 2002/0087151 A1* | 7/2002 | Mody et al. | 606/15 |
| 2004/0073256 A1 | 4/2004 | Marchitto et al. | |
| 2005/0033278 A1 | 2/2005 | McClurken et al. | |
| 2006/0116675 A1 | 6/2006 | McClurken et al. | |
| 2006/0161201 A1* | 7/2006 | Phan et al. | 606/205 |
| 2006/0217706 A1* | 9/2006 | Lau et al. | 606/45 |
| 2009/0318914 A1* | 12/2009 | Utley et al. | 606/33 |
| 2010/0222773 A1* | 9/2010 | Heim et al. | 606/32 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009 317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.

(56) References Cited

OTHER PUBLICATIONS

Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

INDUCTION SEALING

BACKGROUND

1. Technical Field

The present disclosure relates to an electrosurgical instrument and method for sealing tissue. More particularly, the present disclosure relates to an electrosurgical tool having opposing jaw members that include an induction coil and a ferrous layer configured to treat tissue by inductive heating.

2. Background of the Related Art

Electrosurgical forceps utilize mechanical clamping action along with electrical energy to effect hemostasis on the clamped tissue. The forceps (open, laparoscopic or endoscopic) include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

Conventional tissue sealing procedures require imparting electrosurgical energy to an end effector having a pair of opposing jaw members. The combination of heat generated in the opposing jaw members as well as the pressure applied by the jaw members seals the tissue grasped in between jaw members. However, such methods may be inefficient in that all the heat generated in the end effector may not be transferred to tissue. Further, when the end effector is heated during application of energy, once energy application is ceased, the end effector takes time to cool down which may affect tissue disposed between the jaw members.

SUMMARY

In an embodiment of the present disclosure, an end effector assembly is provided. The end effector assembly includes a first jaw member having a support base and a sealing plate formed from a ferrous material. The end effector assembly also includes a second jaw member having a support base, an electrical jaw lead and a sealing plate coupled to the electrical jaw lead. The sealing plate having a first layer formed from a non-stick material and a second layer having a coil formed thereon.

The non-stick material may be formed from glass. The second layer includes a flex circuit where the coil is coupled to a flexible plastic substrate. The electrical jaw lead may be ultrasonically welded to the coil of the sealing plate.

In another embodiment of the present disclosure, an electrosurgical instrument for sealing tissue is provided. The electrosurgical instrument may include a housing having at least one shaft extending therefrom, a handle assembly operably associated with the housing, a rotating assembly operably associated with the housing and configured to rotate the at least one shaft, and an end effector assembly operably coupled to a distal end of the at least one shaft. The end effector assembly includes a first jaw member having a support base and a sealing plate formed from a ferrous material. The end effector assembly also includes a second jaw member having a support base, an electrical jaw lead and a sealing plate coupled to the electrical jaw lead. The sealing plate having a first layer formed from a non-stick material and a second layer having a coil formed thereon.

In yet another embodiment of the present disclosure, an end effector assembly is provided. The end effector assembly includes a first jaw member having a support base and a sealing plate formed from a ferrous material. The end effector assembly also includes a second jaw member having a support base, an electrical jaw lead and a sealing plate coupled to the electrical jaw lead. The sealing plate includes a first layer formed from a non-stick material, a pair of flex circuits where each flex circuit includes a coil formed thereon and at least one insulative layer disposed between the pair of flex circuits.

A first flex circuit in the pair of flex circuits has a first coil and a second flex circuit in the pair flex circuits has a second coil. The first coil and the second coil exhibit similar properties when energy is applied to each coil or different properties when energy is applied to each coil.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the clinician and the term "distal" refers to the end of the apparatus which is further away from the clinician. The term "clinician" refers to any medical professional (i.e., doctor, surgeon, nurse, or the like) performing a medical procedure involving the use of embodiments described herein.

As described in more detail below with reference to the accompanying figures, the present disclosure is directed to the use of an induction coil in a vessel sealing procedure. More specifically, one jaw member of an end effector has a sealing plate with an inductor or coil covered by an isolative non-stick material on top, such as glass. Heat for sealing would be generated by passing electricity through the coil and moving a mating jaw made from a ferrous material in place. In this method, electricity does not pass through tissue. Heat from induction heating and pressure from the mating jaw member causes the sealing effect in tissue. Further, the sealing plates stay cool to the touch, thereby reducing possible unwanted tissue effects. This results in an increase in efficiency and speed of the seal leading to a better outcome for the patient.

Figure 1:
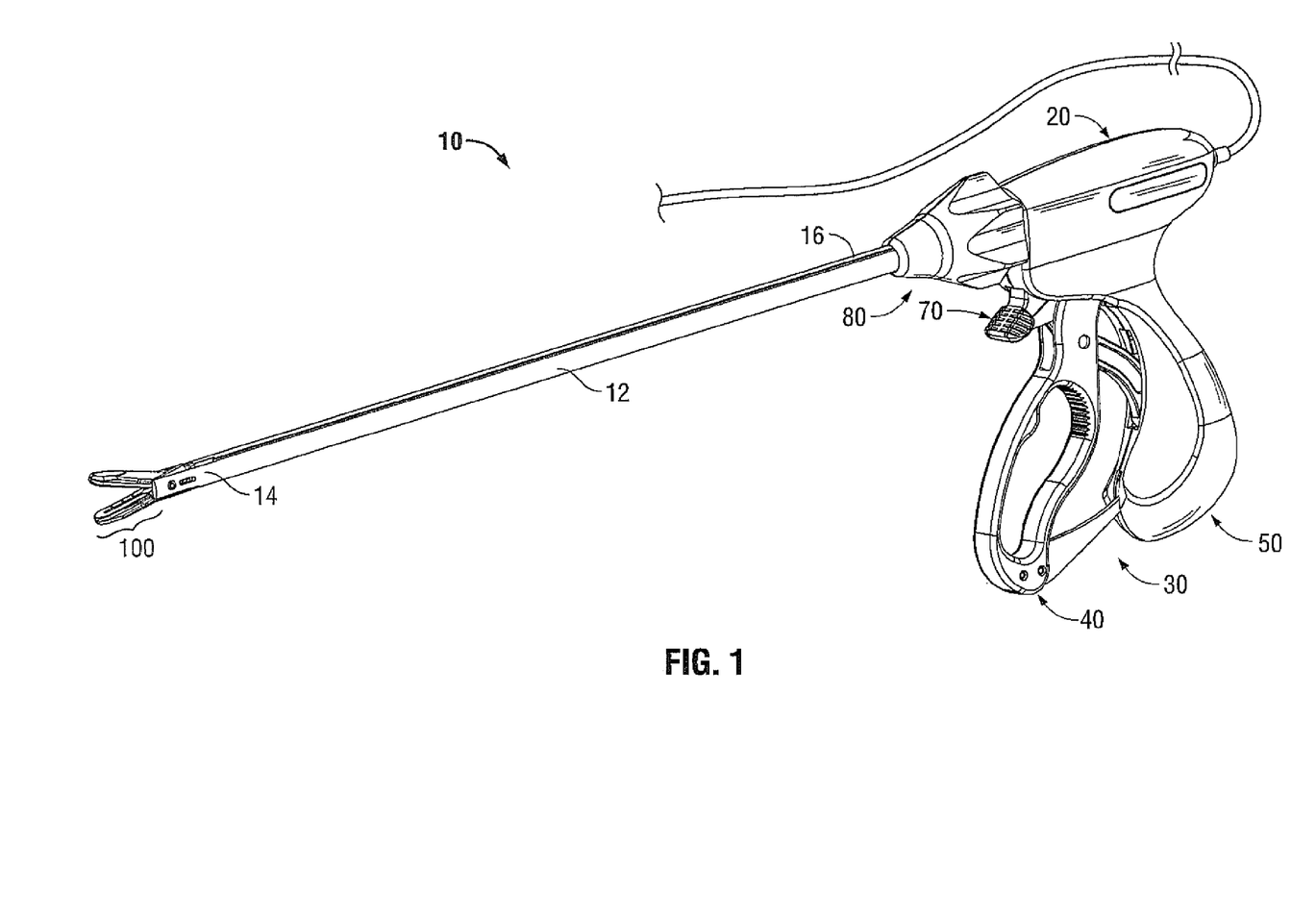
FIG. 1 is a perspective view of an endoscopic bipolar forceps in accordance with an embodiment of the present disclosure.

Turning to FIG. 1, an instrument generally identified as forceps 10 is for use with various surgical procedures and includes a housing 20, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 20. The end effector assembly 100 includes opposing jaw members 110 and 120, which cooperate to effectively grasp tissue for sealing purposes. The end effector assembly 100 is a bilateral assembly, i.e., both jaw members 110 and 120 pivot relative to one another about a pivot pin 95. Unilateral jaw members may also be contemplated. The jaw members 110 and 120 are curved to facilitate manipulation of tissue and to provide better "line of sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156, 846) entitled "VESSEL SEALER AND DIVIDER FOR USE WITH SMALL TROCARS AND CANNULAS.

Figure 2:
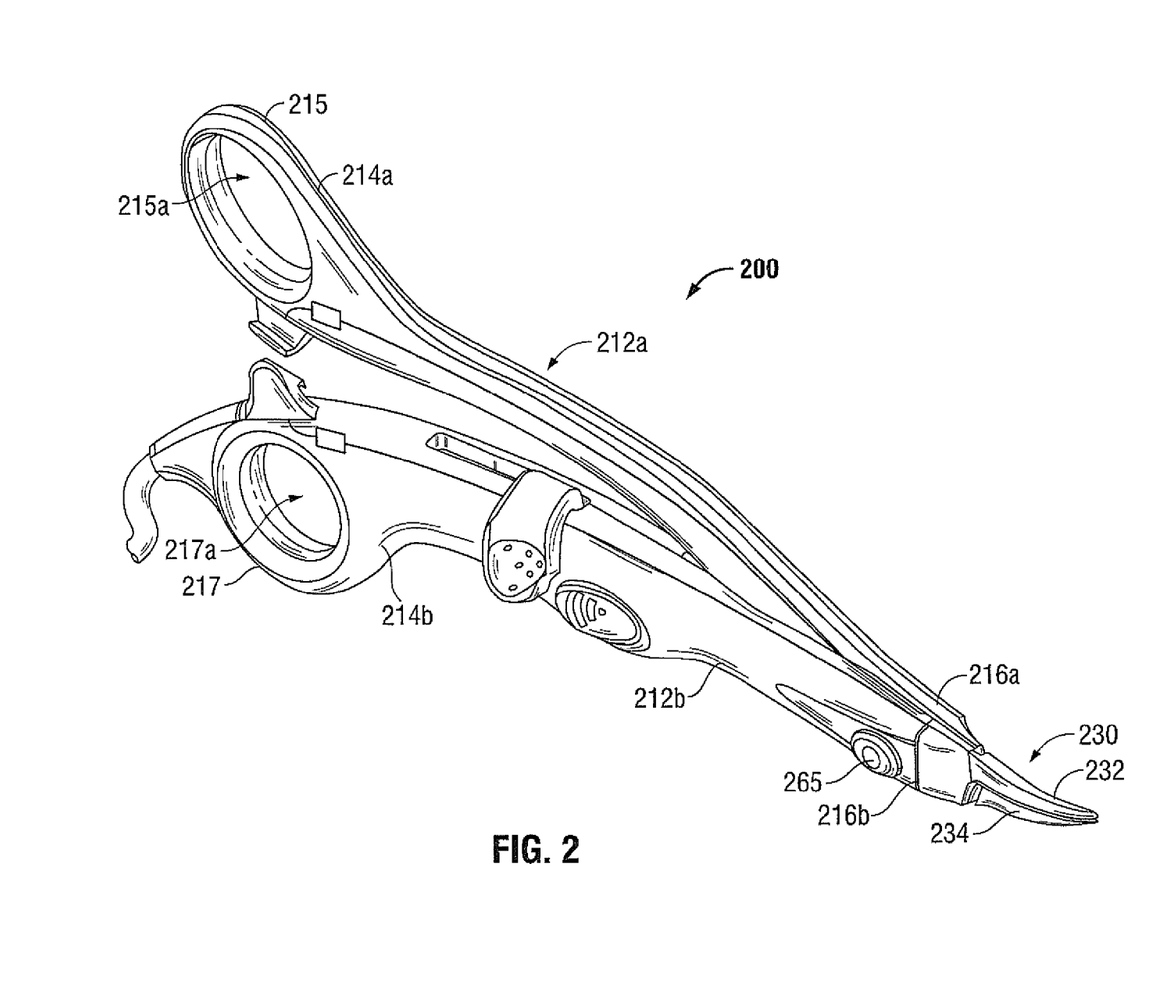
FIG. 2 is a perspective view of an open bipolar forceps in accordance with an embodiment of the present disclosure.

With regard to FIG. 2, an open forceps 200 for use with various surgical procedures is shown. Forceps 200 includes a pair of opposing shafts 212a and 212b having an end effector assembly 230 attached to the distal ends 216a and 216b thereof, respectively. End effector assembly 230 is similar in design to end effector assembly 100 and includes pair of opposing jaw members 232 and 234 that are pivotably connected about a pivot pin 265 and which are movable relative to one another to grasp tissue. Each shaft 212a and 212b includes a handle 215 and 217, respectively, disposed at the proximal end 214a and 214b thereof which each define a finger hole 215a and 217a, respectively, therethrough for receiving a finger of the clinician. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

Figure 3A:
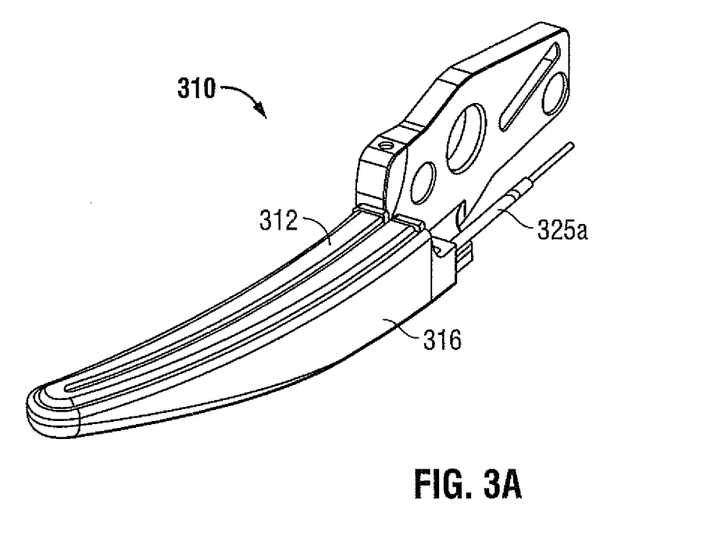
FIGS. 3A and 3B are perspective views of opposing jaw members according to an embodiment of the present disclosure.
Figure 3B:
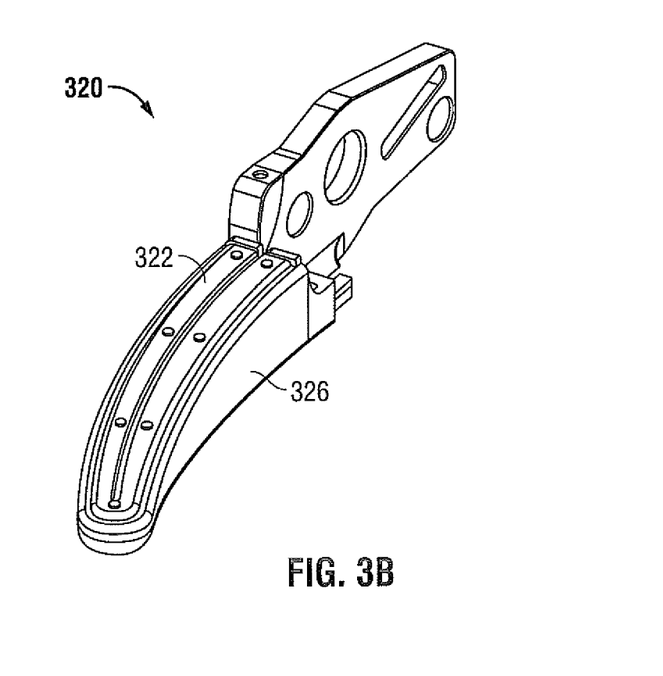

FIGS. 3A and 3B are perspective views of the opposing jaw members 310 and 320. Similar to jaw members 110 and 120, each of the jaw members 310 and 320 include: sealing plates 312 and 322, respectively and support bases 316 and 326 formed as plastic overmolds. Electrical jaw lead 325a supplies energy to an induction coil 524 (FIG. 5B) in jaw members 310. Sealing plate 312 includes a coil as will be described below while sealing plate 322 is made from a ferrous material.

Figure 4A:
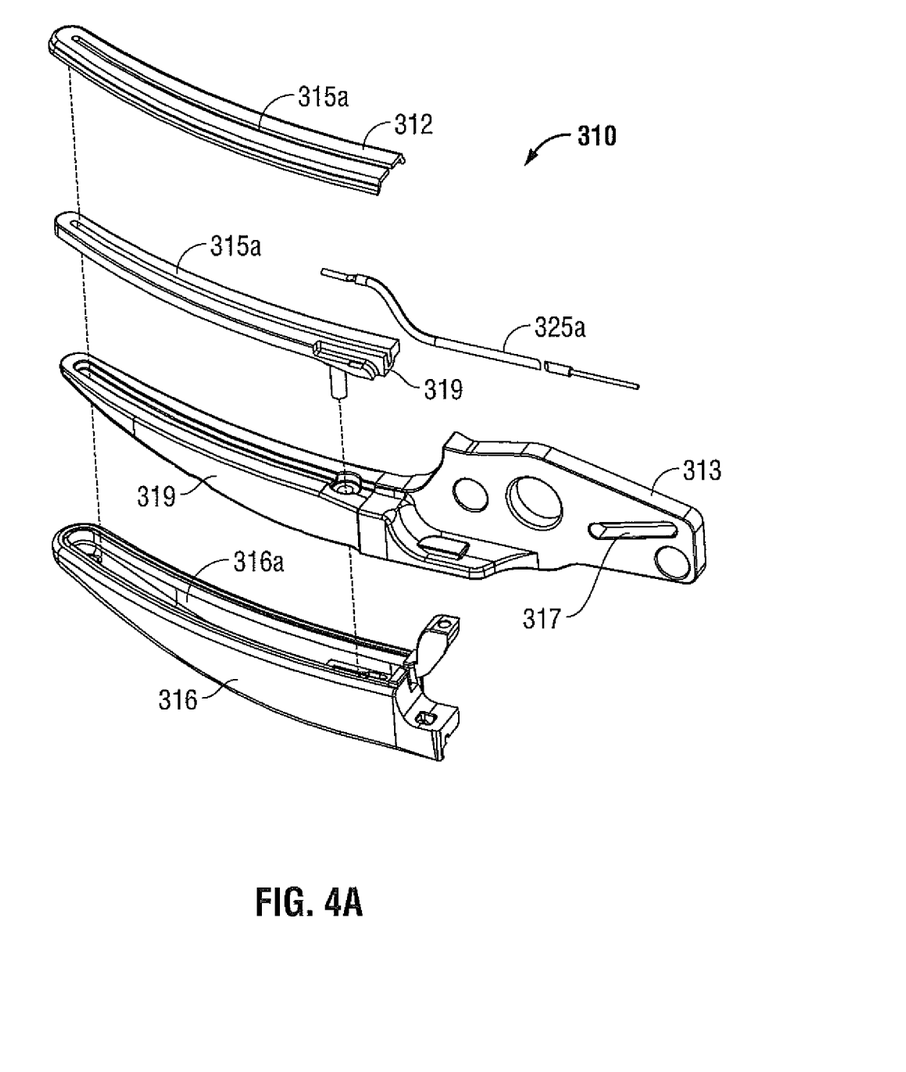
FIGS. 4A and 4B are exploded views of the opposing jaw members of FIGS. 3A and 3B respectively.
Figure 4B:
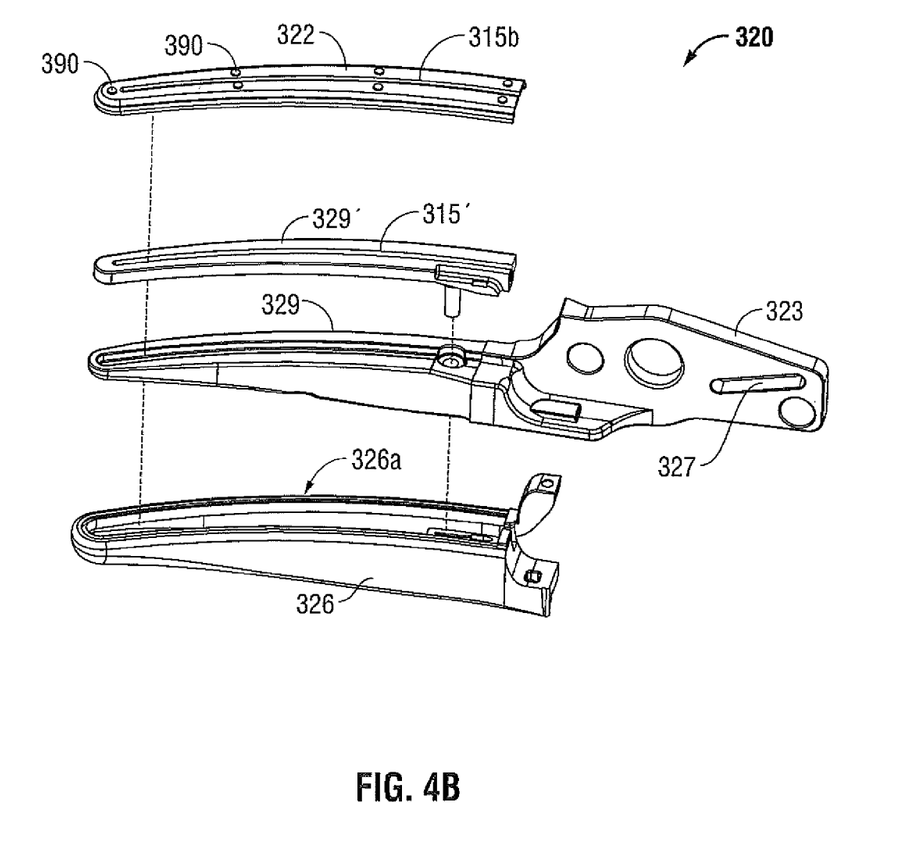

Turning to FIGS. 4A and 4B, the opposing jaw members 310 and 320 include support bases 316 and 326 that each extend distally from flanges 313 and 323, respectively. The support bases 316 and 326 are dimensioned to support insulative plates 319' and 329', which in turn, support electrically conductive sealing plates 312 and 322 thereon. It is contemplated that sealing plates 312 and 322 may be affixed atop the insulative plates 319' and 329', respectively, and support bases 319 and 329, respectively, in any suitable manner, such as snap-fit, over-molding, stamping, ultrasonically welded, etc. The support bases 319 and 329, insulative plates 319' and 329', and sealing plates 312 and 322 are encapsulated by the outer insulative housings 316 and 326 by way of a subsequent overmolding process. Jaw member 310 is connected via an ultrasonic weld to electrical jaw lead 325a.

The jaw members 310 and 320 also include proximal flanges 313 and 323 extending proximally from the support bases 319 and 329, respectively, each of which includes an elongated angled cam slot 317 and 327, respectively, defined therethrough. The jaw member 320 may also include a series of stop members 390 disposed on the inner facing surface of an electrically conductive sealing plate 312 to define a gap between opposing jaw members 310 and 320 during sealing and cutting of tissue. The series of stop members 390 are applied onto the sealing plate 312 during manufacturing. Likewise, the sealing plates 312 and 322 and the insulator plates 319' and 329' include respective longitudinally-oriented knife slots 315a, 315a' and 315b, 315b', respectively, defined therethrough for reciprocation of the knife blade (not shown).

Figures 5A, 5B:
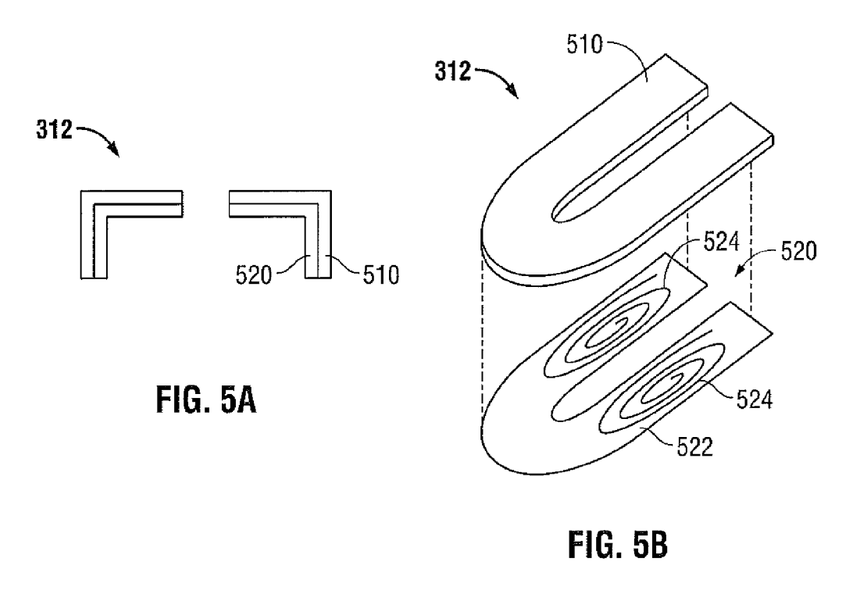
FIG. 5A is a side view of a sealing plate according to an embodiment of the present disclosure.
FIG. 5B is an exploded view of the sealing plate of FIG. 5A.

Turning to FIGS. 5A and 5B, a sealing plate generally designated as 312 is shown. Sealing plate 312 has an outer layer 510 formed from an isolative non-stick material, such as glass. Layer 520 may be a flex circuit having a coil 524 formed on a flexible plastic substrate 522. Such flexible plastic substrates 522 may be formed from, but are not limited to, polyimide, polyether ether ketone (PEEK) film or polylaminate. Flex circuits may also be constructed by screen printing silver circuits onto polyester.

Coil 524 may be made from copper, silver, or any other electrical conductor. Coil 524 may be formed by any suitable method. For instance, coil 524 may be formed by adhering a conductive layer to flexible plastic substrate 522. Using photolithography, a mask outlining coil 524 may be formed and then the conductive layer may be etched to leave coil 524. Electrical jaw lead 325a is ultrasonically welded to coil 524.

When energy is applied to coil 524 in sealing plate 312 and sealing plate 322 is positioned within an electromagnetic field caused by the application of energy to coil 524, heat is generated in tissue disposed between jaw members 310 and 320. Jaw members 310 and 320 may have one or more coatings of a non-stick material. Therefore, tissue would not touch hot metal surfaces and sticking would be reduced. Further, since no heat energy would be applied to the jaws (heat is generated in the tissue) the efficiency and speed of the seal would increase.

Figure 6A:
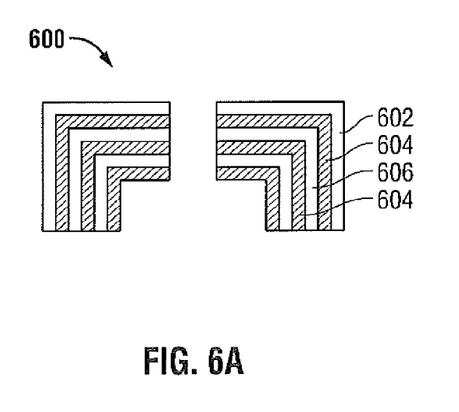
FIG. 6A is a side view of a sealing plate according to another embodiment of the present disclosure.
Figure 6B:
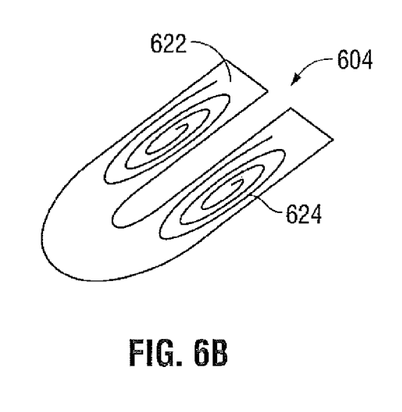
FIG. 6B is a perspective view of a flex circuit included in the sealing plate of FIG. 6A.

Turning to FIGS. 6A and 6B, a sealing plate according to another embodiment of the present disclosure is shown generally as 600. Sealing plate 600 has an outer layer 602 made from an isolative non-stick material, such as glass. Below outer layer 602 are multiple layers of flex circuits 604 and glass or insulative layers 606. Each flex circuit 604 is made in a similar manner as flex circuit 524. Each flex circuit may includes a flexible plastic substrate 622 and a coil 620.

Each flex circuit 604 may have a coil that exhibits similar properties or each flex circuit 604 may have different coils that exhibit different properties when energy is applied to each individual coil. Such properties may include, but are not limited to, size of the electromagnetic field, shape of the magnetic field, amount of energy generated by the electric field, etc. By providing multiple flex circuits, a clinician can control how much heat should be applied to tissue. Depending on which flex circuit is provided with energy or the number of flex circuits provided with energy a clinician may increase or reduce the amount of heat generated. For instance, if energy is applied to a flex circuit with a larger coil instead of a smaller coil, more heat may be generated in tissue. Alternatively, if energy is applied to a single coil instead of multiple coils, less heat may be generated in the tissue.

Figure 7:
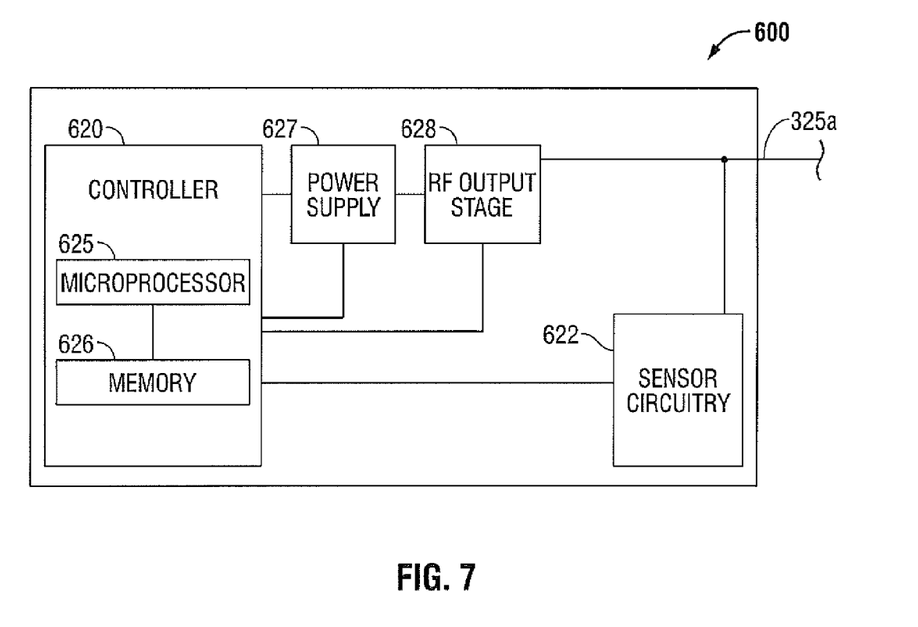
FIG. 7 is a schematic block diagram of an electrosurgical system according to an embodiment of the present disclosure.

FIG. 7 shows a schematic block diagram of the generator 600 having a controller 620, a power supply 627, an RF output stage 628, and a sensor module 622. The power supply 627 provides DC power to the RF output stage 628 which then converts the DC power into RF energy and delivers the RF energy to the instrument 10 and end effector 100. The controller 620 includes a microprocessor 625 having a memory 626 which may be volatile type memory (e.g., RAM) and/or non-volatile type memory (e.g., flash media, disk media, etc.). The microprocessor 625 includes an output port connected to the power supply 627 and/or RF output stage 628 that allows the microprocessor 625 to control the output of the generator 600 according to either open and/or closed control loop schemes.

A closed loop control scheme generally includes a feedback control loop wherein the sensor module 622 provides feedback to the controller 24 (i.e., information obtained from one or more sensing mechanisms for sensing various tissue parameters such as tissue impedance, tissue temperature, output current and/or voltage, etc.). The controller 620 then signals the power supply 627 and/or RF output stage 628 which then adjusts the DC and/or RF power supply, respectively. The controller 620 also receives input signals from the input controls of the generator 600 and/or instrument 10. The controller 620 utilizes the input signals to adjust the power output of the generator 600 and/or instructs the generator 20 to perform other control functions.

The microprocessor 625 is capable of executing software instructions for processing data received by the sensor module 622, and for outputting control signals to the generator 600, accordingly. The software instructions, which are executable by the controller 620, are stored in the memory 626 of the controller 620.

The controller 620 may include analog and/or logic circuitry for processing the sensed values and determining the control signals that are sent to the generator 600, rather than, or in combination with, the microprocessor 625.

The sensor module 622 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 620. The sensor module 622 may include control circuitry that receives information from multiple sensors, and provides the information and the source of the information (e.g., the particular sensor providing the information) to the controller 620.

More particularly, the sensor module 622 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The generator 600 includes suitable input controls (e.g., buttons, activators, switches, touch screen, etc.) for controlling the generator 600, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 10 may include a plurality of input controls which may be redundant with certain input controls of the generator 600. Placing the input controls at the instrument 10 allows for easier and faster modification of RF energy parameters during the surgical procedure without requiring interaction with the generator 600.

A generator 600 according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

The foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached figures are presented only to demonstrate certain examples of the disclosure. Other elements, steps, methods and techniques that are insubstantially different from those described above and/or in the appended claims are also intended to be within the scope of the disclosure.

What is claimed is:

1. An end effector assembly, comprising:
    a first jaw member having a support base and a sealing plate formed from a ferrous material; and
    a second jaw member comprising:
        a support base;
        an electrical jaw lead; and
        a sealing plate coupled to the electrical jaw lead, the sealing plate having a first layer formed from a non-stick material and a second layer having a planar coil formed thereon.

2. The end effector assembly according to claim 1, wherein the non-stick material is glass.

3. The end effector assembly according to claim 1, wherein the second layer is a flex circuit.

4. The end effector assembly according to claim 1, wherein the electrical jaw lead is ultrasonically welded to the planar coil of the sealing plate.

5. An electrosurgical instrument for sealing tissue, comprising:
    a housing having at least one shaft extending therefrom;
    a handle assembly operably associated with the housing;
    a rotating assembly operably associated with the housing and configured to rotate the at least one shaft;
    an end effector assembly operably coupled to a distal end of the at least one shaft, the end effector comprising:
        a first jaw member having a support base and a sealing plate formed from a ferrous material; and
        a second jaw member comprising:
            a support base;
            an electrical jaw lead; and
            a sealing plate coupled to the electrical jaw lead, the sealing plate having a first layer formed from a non-stick material and a second layer having a planar coil formed thereon.

6. An end effector assembly, comprising:
a first jaw member having a support base and a sealing plate formed from a ferrous material; and
a second jaw member comprising:
   a support base;
   an electrical jaw lead; and
   a sealing plate coupled to the electrical jaw lead, the sealing plate having:
a first layer formed from a non-stick material;
a first flex circuit having a first coil formed thereon;
a second flex circuit having a second coil formed thereon; and
at least one insulative layer disposed between the first flex circuit and the second flex circuit.

7. The end effector assembly according to claim 6, wherein the first coil and the second coil exhibit similar properties when energy is applied to each of the first and second coils.

8. The end effector assembly according to claim 6, wherein the first coil and the second coil exhibit different properties when energy is applied to each of the first and second coils.

* * * * *